United States Patent [19]

Frey et al.

[11] Patent Number: 4,938,770

[45] Date of Patent: Jul. 3, 1990

[54] STEM FOR A FEMORAL HEAD PROSTHESIS

[75] Inventors: Otto Frey, Winterthur; Rudolf Koch, Berlingen, both of Switzerland

[73] Assignee: Sulzer Brothers Limited, Winterthur, Switzerland

[21] Appl. No.: 416,515

[22] Filed: Oct. 3, 1989

[30] Foreign Application Priority Data

Oct. 27, 1988 [CH] Switzerland .......................... 4001/88

[51] Int. Cl.⁵ ............................................... A61F 2/36
[52] U.S. Cl. ........................................ 623/23; 623/16; 623/18
[58] Field of Search .................... 623/23, 22, 16, 18, 623/20

[56] References Cited

U.S. PATENT DOCUMENTS

| | | | |
|---|---|---|---|
| 3,979,779 | 9/1976 | Zeibig et al. | 623/16 X |
| 4,266,302 | 5/1981 | Tornier | 623/23 |
| 4,516,277 | 5/1985 | Butel | 623/23 |
| 4,743,263 | 5/1988 | Petrtyl et al. | 623/23 |

FOREIGN PATENT DOCUMENTS

| | | | |
|---|---|---|---|
| 0190446 | 8/1986 | European Pat. Off. | 623/23 |
| 0257222 | 3/1988 | European Pat. Off. | |
| 3406358 | 12/1984 | Fed. Rep. of Germany | 623/23 |
| 3536895 | 5/1986 | Fed. Rep. of Germany | 623/23 |
| 2290881 | 6/1976 | France . | |
| 2610823 | 8/1988 | France | 623/23 |
| 2070939 | 9/1981 | United Kingdom . | |

Primary Examiner—Ronald L. Frinks
Attorney, Agent, or Firm—Kenyon & Kenyon

[57] ABSTRACT

The cavity of the stem of the tumor or re-operation prosthesis is subdivided by support elements into sub-cavities filled with bony material. The support elements are formed with central apertures through which the bony material can be supplied and re-vascularized from the living bone tissue of the femur stump. Wire mesh may cover over the apertures in the support elements as well as the slots between the circumferentially disposed webs which define the cavity of the stem.

12 Claims, 2 Drawing Sheets

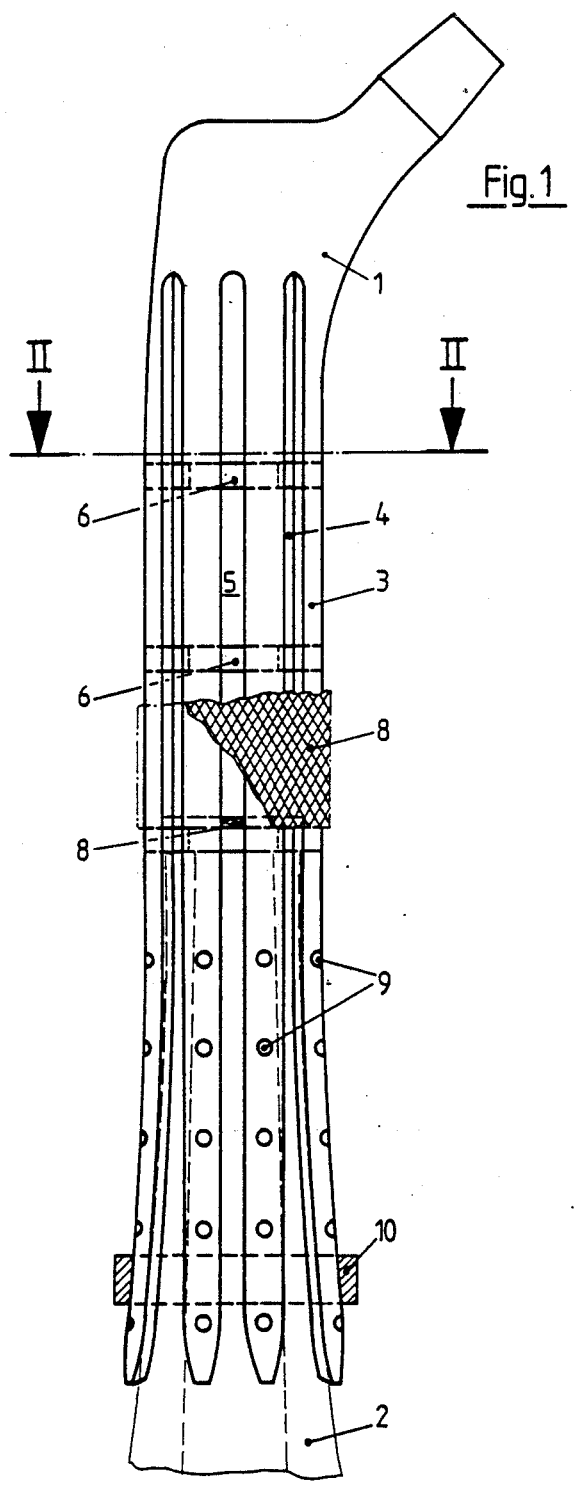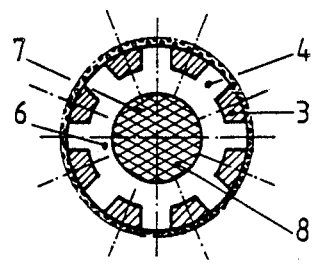

STEM FOR A FEMORAL HEAD PROSTHESIS

This invention relates to a stem for a femoral head prosthesis.

Heretofore, various types of stems have been provided for femoral head prosthesis. For example, German Patent Application No. 31 13 898 describes a stem which is hollow over at least some of the length thereof with a stem wall in the hollow region consisting of a large number of narrow webs with slots therebetween. In addition, a cavity of the stem, which is to be encased in the bone tissue of a femur as far as the neck of the prosthesis, is subdivided by dowel-like elements into a number of sub-cavities which are filled with bony material in order to boost bone formation. The purpose of the bony material, in addition to electrostimulation, is to boost bone formation and secure the stem in the encasing bone in order to increase bone growth around the discrete webs from the stem-encasing bone.

However, in cases of tumors or re-operations, it has been very often necessary to provide hip joint replacements in which the bony material encasing the stem of the prosthesis is present only partly, if at all in the proximal zone. Such a prosthesis can therefore be fixed on or in the bone only in the distal zone. In such cases, the proximal part of the stem of such a prosthesis is "bone free". As a result, the supply and re-vascularization of bony material in a cavity around which discrete webs extend and which is subdivided by support elements is difficult to accomplish. The supply and revascularization of this bony material by tissue from a distal "stump" of the femur, such tissue first growing on and then through the bony material, is at least impeded, if not prevented by the support elements which form a closed barrier.

Other types of hollowed stems for a femur prosthesis have also been known. For example, U.S. Pat. No. 4,516,277 describes a prosthesis having a rod which is to be engaged in a medullary canal of a femur wherein the rod is composed of longitudinal elements to give the rod flexibility. In addition, distal portions of the rod are connected together by a connecting part. Similar prostheses of hollowed or skeletal construction are also described in European Patent Application No. 0 257 222, French Patent No. 2 610 823 and German OS No. 3 536 895. Still further, European Patent Application No. 0 190 446 describes a prosthesis made entirely of hollow construction while French Patent No. 2 290 881 describes a prosthesis having a hollowed stem for fitting over a femur stump.

Accordingly, it is an object of the invention to facilitate revascularization of a bony material charged into a stem cavity of a hollow prosthesis.

It is another object of the invention to provide a stem for a femoral head prosthesis which is suitable for re-operation or tumors.

It is another object of the invention to improve the construction of a femur head prosthesis stem for re-operations and tumors and to facilitate re-vascularization of bony material within a hollow cavity of the prosthesis.

Briefly, the invention provides a stem for a femoral prosthesis which is comprised of a hollow region defining an internal cavity, a plurality of narrow webs in the hollow region disposed in circumferentially spaced relation to define slots therebetween and a plurality of discoid support elements disposed in longitudinally spaced relation within the internal cavity and in engagement with the webs. In accordance with the invention, each support element is provided with an aperture so that living tissue from a femur stump can invade the internal cavity without hinderance. Thus, the tissue can provide for substantial re-vascularization of bony material filling the internal cavity of the stem.

Advantageously, the apertures in the discoid support elements and/or the slots between the webs can be covered at least to some extent by wire mesh to prevent the bony material from dropping through the apertures and/or slots.

In one embodiment, the stem is constructed so as to be fixed onto a femur stump. In this case, the stem is pushed onto the stump and then rigidly connected thereto. Conveniently, the webs extend to a distal end of the stem and are radially expandable thereat in order to engage about the femur stump. In addition, at least one axially movable clamping ring may be disposed about these webs distally of the support elements for clamping the webs about a femur stump. Also, the webs may be provided with bores in a distal region for receiving bone screws which may be threaded into a femur stump. The stem may also be constructed so as to be inserted into a bone cavity. In this case, the webs are united at the distal end for fitting into the cavity of a femur.

These and other objects and advantages of the invention will become more apparent from the following detailed description taken in conjunction with the accompanying drawings wherein:

FIG. 1 illustrates a diagrammatic side view of a stem for a femoral head prosthesis constructed in accordance with the invention;

FIG. 2 illustrates a view taken on line II—II of FIG. 1; and

Figure 3:
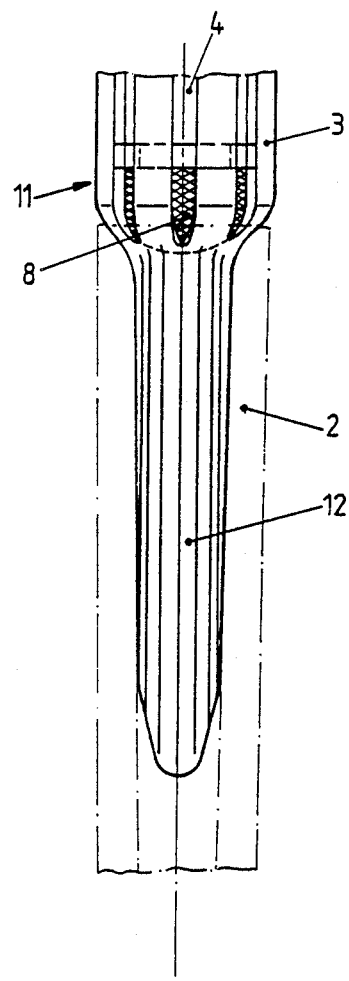
FIG. 3 illustrates a distal end of a modified prosthesis stem in accordance with the invention.

Referring to FIG. 1, the femoral head prosthesis is constructed as a tumor or a re-operation prosthesis and includes a straight stem 1 which can be placed over a femur stump 2 which has been prepared by appropriate surgery. As indicated, the stem 1 has a plurality of narrow discrete webs 3 which are disposed to define a hollow region of the stem 1 and are disposed in circumferentially spaced relation to define slots 4 therebetween. The stem 1 is therefore open at the distal end so as to be placed over the femur stump 2.

As indicated, the webs 3 define an internal cavity 5 which is adapted to receive bone material therein. In addition, a plurality of discoid support elements 6 are distributed in spaced-apart relationship over the height of the cavity 5 and are in engagement with the webs 3 in order to improve stem stability. Referring to FIG. 2, each support elements 6 has a centrally disposed aperture 7 to facilitate axial growth of bony material.

In order to facilitate the filling of the cavity 5 with bony material, the aperture 7 and/or the slots 4 are covered at least to some extent by single-layer or multilayer wire mesh 8 of a size to permit bone growth therethrough in an unhindered manner while the bone material charged into the cavity 5 is retained. The wire mesh 8 which covers the slots 4 may be disposed outside and inside the cavity 5. A preferred mesh size is, for example, from 1 to 1.4 millimeters.

Referring to FIG. 1, the webs 4 extend to the distal end of the stem and are radially expandable thereat so as to engage with the femur stump 2 under pressure. Fixation of the webs 3 may be facilitated by means of bone screws (not shown) which can be threaded through bores 9 in the distal regions of the webs 3. IN addition, fixation of the stem 1 on the femur stump 2 may be improved by the use of at least one axially movable clamping ring 10 disposed about the webs 3 distally of the support elements 6. This ring 10 can be wedged together with the expanded webs 3 by being moved distally as indicated.

In order to mount the stem 1 on the femur stump 2, the cavity 5 is first filled with bone material. Thereafter, the webs 3 are passed about the stump 2 with the webs 3 being expanded radially at the distal ends. The clamping ring 10 is then slid axially in the distal direction to secure the stem to the stump 2 in a friction-fit manner. Screws (not shown) may then be threaded through the respective bores 9. Once implanted, re-vascularization of the bony material may take place from the stump 2 which extends to near the distal-most support element 6.

Referring to FIG. 3, wherein like reference characters indicate like parts as above, the webs 3 of the stem 11 may be introduced into a surgically prepared cavity in a femur 2. In this case, the webs 3 are united at the distal end for fitting into the femur cavity. As indicated, the webs 3 come together to form a compact distal stem zone 12 distally of the distal-most support elements 6. This zone 12, which narrows slightly conically towards the free end, is fixed in a conventional manner in the bone in either an uncemented matter or in a bed of bone cement. The zone 12 may also have a surface structure for promoting the ingrowth an invasion of tissue or the connection to the bone cement.

The supply of bony material in the interior of the stem cavity proceeds in this case outwardly from the stump end into the bone tissue growing through the slots 4, the bone tissue growing at least to some height in the cavity while providing at least some re-vascularization of the bony material present in the cavity.

The invention thus provides a relatively simple structure within a hollow stem of a femoral head prosthesis for re-vascularization of bony material within the cavity of the prosthesis.

What is claimed is:

1. A stem for a femoral head prosthesis comprising
    a hollow region defining an internal cavity;
    a plurality of narrow webs in said hollow region disposed in circumferentially spaced relation to define slots, therebetween; and
    a plurality of discoid support elements disposed in longitudinally spaced relation within said internal cavity and in engagement with said webs, each said support element having an aperture therein.

2. A stem as set forth in claim 1 wherein said web. extend to a distal end thereof and are readily expandable thereat.

3. A stem as set forth in claim 2 further comprising at least one axially movable clamping ring about said webs distally of said support elements for clamping said webs about a femur stump.

4. A stem as set forth in claim 3 wherein at least some of said webs have bores in a distal region for receiving bone screws.

5. A stem as set forth in claim 1 which further comprises a wire mesh covering said aperture of each respective support element, said mesh being of a size to permit bone growth therethrough.

6. A stem as set forth in claim 1 which further comprises a wire mesh covering each slot and being of a size to permit bone growth therethrough.

7. A stem for a femoral head prosthesis comprising
    a plurality of circumferentially disposed narrow webs defining an internal cavity to receive bone material therein, said webs being disposed in spaced relation to define a plurality of slots therebetween;
    a plurality of discoid support elements in supporting engagement with said webs to sub-divide said cavity, each support element having an aperture therein; and
    a wire mesh covering said aperture of at least a distal-most support element, said mesh being of a size to permit bone growth therethrough from a femur stump.

8. A stem as set forth in claim 7 which further comprises a wire mesh covering each slot and being of a size to permit bone growth therethrough.

9. A stem as set forth in claim 7 wherein said webs extend to a distal end thereof and are readily expandable thereat and at least one axially movable clamping ring about said webs distally of said support elements for clamping said webs about a femur stump.

10. A stem as set forth in claim 9 wherein at least some of said webs have bores in a distal region for receiving bone screws.

11. A stem as set forth in claim 4 wherein said webs are united at a distal end for fitting into a cavity of a femur.

12. A stem as set forth in claim 11 which further comprises a wire mesh covering each slot and being of a size to permit bone growth therethrough.

* * * * *

UNITED STATES PATENT AND TRADEMARK OFFICE
CERTIFICATE OF CORRECTION

PATENT NO. : 4,938,770

DATED : July 3, 1990

INVENTOR(S) : OTTO FREY, et al

It is certified that error appears in the above-identified patent and that said Letters Patent is hereby corrected as shown below:

```
Column 2, line 55 change "elements" to -element-
Column 3, line 3 change "IN" to -In-
Column 3, line 31 change "an" to -and-
Column 4, line 3 change "web" to -webs-
```

Signed and Sealed this

Seventeenth Day of December, 1991

Attest:

HARRY F. MANBECK, JR.

*Attesting Officer*      *Commissioner of Patents and Trademarks*